(12) United States Patent
Stahmann et al.

(10) Patent No.: US 8,632,470 B2
(45) Date of Patent: Jan. 21, 2014

(54) ASSESSMENT OF PULMONARY VASCULAR RESISTANCE VIA PULMONARY ARTERY PRESSURE

(75) Inventors: Jeffrey E. Stahmann, Ramsey, MN (US); Krzysztof Z. Siejko, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1085 days.

(21) Appl. No.: 12/566,432

(22) Filed: Sep. 24, 2009

(65) Prior Publication Data

US 2010/0125211 A1 May 20, 2010

Related U.S. Application Data

(60) Provisional application No. 61/116,174, filed on Nov. 19, 2008.

(51) Int. Cl.
*A61B 5/02* (2006.01)
(52) U.S. Cl.
USPC ............ 600/486; 600/481; 600/483; 600/485
(58) Field of Classification Search
USPC .................................. 600/481, 483, 485, 486
See application file for complete search history.

(56) References Cited

U.S. PATENT DOCUMENTS

| | | | |
|---|---|---|---|
| 3,310,885 A | 3/1967 | Alderson | |
| 3,320,946 A | 5/1967 | Dethloff et al. | |
| 3,536,836 A | 10/1970 | Pfeiffer | |
| 3,568,661 A | 3/1971 | Franklin | |
| 3,672,352 A | 6/1972 | Summers | |
| 3,692,027 A | 9/1972 | Ellinwood | |
| 3,757,770 A | 9/1973 | Brayshaw et al. | |
| 3,794,840 A | 2/1974 | Scott | |
| 3,943,915 A | 3/1976 | Severson | |
| 4,003,379 A | 1/1977 | Ellinwood | |
| 4,041,954 A | 8/1977 | Ohara | |
| 4,127,110 A | 11/1978 | Bullara | |

(Continued)

FOREIGN PATENT DOCUMENTS

| | | |
|---|---|---|
| EP | 0897690 | 2/1999 |
| EP | 0928598 | 7/1999 |

(Continued)

OTHER PUBLICATIONS

Garg et al. "Jugular Venous Pulse: An Appraisal", Journal, Indian Academy of Clinical Medicine. vol. 1, No. 3, Oct.-Dec. 2000. p. 260-269.*

(Continued)

*Primary Examiner* — Patricia Mallari
*Assistant Examiner* — Christian Jang
(74) *Attorney, Agent, or Firm* — Faegre Baker Daniels LLP

(57) ABSTRACT

Methods and systems for assessing pulmonary or systemic vascular resistance in a patient using pressure measurements are disclosed. An illustrative method of measuring pulmonary vascular resistance includes electrically inducing a retrograde pressure pulse within the heart, sensing at least one arterial pressure parameter in response to the retrograde pressure pulse using a pressure sensor located within a pulmonary artery, and computing a value of the pulmonary vascular resistance using the at least one sensed arterial pressure parameter. Data from multiple pulmonary vascular resistance assessments can be taken over an extended period of time within the patient to aid in detecting an underlying cardiac or pulmonary condition such as cardiogenic pulmonary edema.

22 Claims, 6 Drawing Sheets

(56) References Cited

U.S. PATENT DOCUMENTS

| | | |
|---|---|---|
| 4,146,029 A | 3/1979 | Ellinwood |
| 4,223,801 A | 9/1980 | Carlson |
| 4,227,407 A | 10/1980 | Drost |
| 4,237,900 A | 12/1980 | Schulman et al. |
| 4,281,664 A | 8/1981 | Duggan |
| 4,360,019 A | 11/1982 | Portner et al. |
| 4,407,296 A | 10/1983 | Anderson |
| 4,450,527 A | 5/1984 | Sramek |
| 4,480,483 A | 11/1984 | McShane |
| 4,519,401 A | 5/1985 | Ko et al. |
| 4,541,431 A | 9/1985 | Ibrahim et al. |
| 4,543,955 A | 10/1985 | Schroeppel |
| 4,550,370 A | 10/1985 | Baker |
| 4,585,004 A | 4/1986 | Brownlee |
| 4,593,703 A | 6/1986 | Cosman |
| 4,600,855 A | 7/1986 | Strachan |
| 4,616,640 A | 10/1986 | Kaali et al. |
| 4,651,740 A | 3/1987 | Schroeppel |
| 4,653,508 A | 3/1987 | Cosman |
| 4,660,568 A | 4/1987 | Cosman |
| 4,676,255 A | 6/1987 | Cosman |
| 4,677,985 A | 7/1987 | Bro et al. |
| 4,680,957 A | 7/1987 | Dodd |
| 4,686,987 A | 8/1987 | Salo et al. |
| 4,697,595 A | 10/1987 | Breyer et al. |
| 4,719,921 A | 1/1988 | Chirife |
| 4,768,176 A | 8/1988 | Kehr et al. |
| 4,768,177 A | 8/1988 | Kehr et al. |
| 4,781,715 A | 11/1988 | Wurzel |
| 4,791,936 A | 12/1988 | Snell et al. |
| 4,793,825 A | 12/1988 | Benjamin et al. |
| 4,809,697 A | 3/1989 | Causey, III et al. |
| 4,845,503 A | 7/1989 | Adam et al. |
| 4,846,191 A | 7/1989 | Brockway et al. |
| 4,854,327 A | 8/1989 | Kunig |
| 4,899,752 A | 2/1990 | Cohen |
| 4,909,259 A | 3/1990 | Tehrani |
| 4,945,914 A | 8/1990 | Allen |
| 4,967,749 A | 11/1990 | Cohen |
| 4,986,270 A | 1/1991 | Cohen |
| 4,991,579 A | 2/1991 | Allen |
| 4,995,068 A | 2/1991 | Chou et al. |
| 4,995,398 A | 2/1991 | Turnidge |
| 5,003,976 A | 4/1991 | Alt |
| 5,024,224 A | 6/1991 | Engebretson |
| 5,025,795 A | 6/1991 | Kunig |
| 5,029,582 A | 7/1991 | Lekholm |
| 5,040,536 A | 8/1991 | Riff |
| 5,040,538 A | 8/1991 | Mortazavi |
| 5,113,859 A | 5/1992 | Funke |
| 5,139,020 A | 8/1992 | Koestner et al. |
| 5,154,171 A | 10/1992 | Chirife |
| 5,161,536 A | 11/1992 | Vilkomerson et al. |
| 5,163,429 A | 11/1992 | Cohen |
| 5,178,151 A | 1/1993 | Sackner |
| 5,178,153 A | 1/1993 | Einzig |
| 5,183,051 A | 2/1993 | Kraidin et al. |
| 5,188,106 A | 2/1993 | Nappholz et al. |
| 5,190,035 A | 3/1993 | Salo et al. |
| 5,199,428 A | 4/1993 | Obel et al. |
| 5,200,891 A | 4/1993 | Kehr et al. |
| 5,213,098 A | 5/1993 | Bennett et al. |
| 5,246,008 A | 9/1993 | Mueller |
| 5,265,615 A | 11/1993 | Frank et al. |
| 5,267,174 A | 11/1993 | Kaufman et al. |
| 5,277,191 A | 1/1994 | Hughes |
| 5,279,309 A | 1/1994 | Taylor et al. |
| 5,279,607 A | 1/1994 | Schentag et al. |
| 5,289,821 A | 3/1994 | Swartz |
| 5,300,092 A | 4/1994 | Schaldach |
| 5,314,457 A | 5/1994 | Jeutter et al. |
| 5,329,459 A | 7/1994 | Kaufman et al. |
| 5,330,505 A | 7/1994 | Cohen |
| 5,339,051 A | 8/1994 | Koehler et al. |
| 5,368,040 A | 11/1994 | Carney |
| 5,375,603 A | 12/1994 | Feiler |
| 5,394,457 A | 2/1995 | Leibinger et al. |
| 5,397,329 A | 3/1995 | Allen |
| 5,400,793 A | 3/1995 | Wesseling |
| 5,411,535 A | 5/1995 | Fujii et al. |
| 5,411,551 A | 5/1995 | Winston et al. |
| 5,417,717 A | 5/1995 | Salo et al. |
| 5,423,323 A | 6/1995 | Orth |
| 5,423,334 A | 6/1995 | Jordan |
| 5,438,990 A | 8/1995 | Wahlstrand et al. |
| 5,445,608 A | 8/1995 | Chen et al. |
| 5,454,838 A | 10/1995 | Vallana et al. |
| 5,469,859 A | 11/1995 | Tsoglin et al. |
| 5,476,488 A | 12/1995 | Morgan et al. |
| 5,488,954 A | 2/1996 | Sleva et al. |
| 5,490,962 A | 2/1996 | Cima et al. |
| 5,509,424 A | 4/1996 | Al-Ali |
| 5,528,067 A | 6/1996 | Farb |
| 5,535,752 A | 7/1996 | Halperin et al. |
| 5,558,091 A | 9/1996 | Acker et al. |
| 5,562,714 A | 10/1996 | Grevious |
| 5,564,434 A | 10/1996 | Halperin et al. |
| 5,571,152 A | 11/1996 | Chen et al. |
| 5,604,531 A | 2/1997 | Iddan et al. |
| 5,605,154 A | 2/1997 | Ries et al. |
| 5,619,997 A | 4/1997 | Kaplan |
| 5,626,630 A | 5/1997 | Markowitz et al. |
| 5,628,782 A | 5/1997 | Myers |
| 5,642,731 A | 7/1997 | Kehr |
| 5,643,327 A | 7/1997 | Dawson et al. |
| 5,647,369 A | 7/1997 | Petrucelli et al. |
| 5,656,428 A | 8/1997 | McAllister et al. |
| 5,704,352 A | 1/1998 | Tremblay et al. |
| 5,705,753 A | 1/1998 | Hastings et al. |
| 5,728,281 A | 3/1998 | Holmstrom et al. |
| 5,729,129 A | 3/1998 | Acker |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,749,909 A | 5/1998 | Schroeppel et al. |
| 5,752,235 A | 5/1998 | Kehr et al. |
| 5,752,976 A | 5/1998 | Duffin et al. |
| 5,755,766 A | 5/1998 | Chastain et al. |
| 5,769,877 A | 6/1998 | Barreras, Sr. |
| 5,776,324 A | 7/1998 | Usala |
| 5,792,195 A | 8/1998 | Carlson et al. |
| 5,796,827 A | 8/1998 | Coppersmith et al. |
| 5,797,395 A | 8/1998 | Martin |
| 5,800,478 A | 9/1998 | Chen et al. |
| 5,807,258 A | 9/1998 | Cimochowski et al. |
| 5,807,395 A | 9/1998 | Mulier et al. |
| 5,807,397 A | 9/1998 | Barreras |
| 5,810,009 A | 9/1998 | Mine et al. |
| 5,810,735 A | 9/1998 | Halperin et al. |
| 5,832,924 A | 11/1998 | Archibald et al. |
| 5,833,603 A | 11/1998 | Kovacs et al. |
| 5,835,455 A | 11/1998 | Hanson et al. |
| 5,836,300 A | 11/1998 | Mault |
| 5,843,135 A | 12/1998 | Weijand et al. |
| 5,855,609 A | 1/1999 | Knapp |
| 5,856,722 A | 1/1999 | Haronian et al. |
| 5,868,673 A | 2/1999 | Vesely |
| 5,873,835 A | 2/1999 | Hastings et al. |
| 5,886,267 A | 3/1999 | Ortiz |
| 5,891,180 A | 4/1999 | Greeninger et al. |
| 5,904,708 A | 5/1999 | Goedeke et al. |
| 5,911,685 A | 6/1999 | Siess et al. |
| 5,919,221 A | 7/1999 | Miesel |
| 5,941,249 A | 8/1999 | Maynard |
| 5,954,641 A | 9/1999 | Kehr et al. |
| 5,957,950 A | 9/1999 | Mockros et al. |
| 5,967,986 A | 10/1999 | Cimochowski et al. |
| 5,979,898 A | 11/1999 | Pan |
| 6,002,963 A | 12/1999 | Mouchawar et al. |
| 6,023,641 A | 2/2000 | Thompson |
| 6,024,704 A | 2/2000 | Meador et al. |
| 6,050,951 A | 4/2000 | Friedman et al. |
| 6,053,873 A | 4/2000 | Govari et al. |
| 6,083,248 A | 7/2000 | Thompson |

(56) References Cited

U.S. PATENT DOCUMENTS

| | | |
|---|---|---|
| 6,112,116 A | 8/2000 | Fischell et al. |
| 6,123,861 A | 9/2000 | Santini, Jr. et al. |
| 6,140,740 A | 10/2000 | Porat et al. |
| 6,141,588 A | 10/2000 | Cox et al. |
| 6,152,885 A | 11/2000 | Taepke |
| 6,155,267 A | 12/2000 | Nelson |
| 6,161,032 A | 12/2000 | Acker |
| 6,162,238 A | 12/2000 | Kaplan et al. |
| 6,171,252 B1 | 1/2001 | Roberts |
| 6,179,767 B1 | 1/2001 | Ziegler et al. |
| 6,185,452 B1 | 2/2001 | Schulman et al. |
| 6,198,965 B1 | 3/2001 | Penner et al. |
| 6,200,265 B1 | 3/2001 | Walsh et al. |
| 6,234,973 B1 | 5/2001 | Meador et al. |
| 6,236,889 B1 | 5/2001 | Soykan et al. |
| 6,237,398 B1 | 5/2001 | Porat et al. |
| 6,239,724 B1 | 5/2001 | Doron et al. |
| 6,248,080 B1 | 6/2001 | Miesel et al. |
| 6,256,538 B1 | 7/2001 | Ekwall |
| 6,266,567 B1 | 7/2001 | Ishikawa et al. |
| 6,273,904 B1 | 8/2001 | Chen et al. |
| 6,277,078 B1 | 8/2001 | Porat et al. |
| 6,278,894 B1 | 8/2001 | Salo et al. |
| 6,298,267 B1 | 10/2001 | Rosborough et al. |
| 6,305,381 B1 | 10/2001 | Weijand et al. |
| 6,308,099 B1 | 10/2001 | Fox et al. |
| 6,314,323 B1 | 11/2001 | Ekwall |
| 6,330,957 B1 | 12/2001 | Bell-Greenstreet |
| 6,331,163 B1 | 12/2001 | Kaplan |
| 6,368,275 B1 | 4/2002 | Sliwa et al. |
| 6,394,958 B1 | 5/2002 | Bratteli et al. |
| 6,397,661 B1 | 6/2002 | Grimes et al. |
| 6,409,674 B1 | 6/2002 | Brockway et al. |
| 6,409,675 B1 | 6/2002 | Turcott |
| 6,411,850 B1 | 6/2002 | Kay et al. |
| 6,416,474 B1 | 7/2002 | Penner et al. |
| 6,421,565 B1 | 7/2002 | Hemmingsson |
| 6,431,175 B1 | 8/2002 | Penner et al. |
| 6,432,050 B1 | 8/2002 | Porat et al. |
| 6,438,408 B1 | 8/2002 | Mulligan et al. |
| 6,441,747 B1 | 8/2002 | Khair et al. |
| 6,442,413 B1 | 8/2002 | Silver |
| 6,445,953 B1 | 9/2002 | Bulkes et al. |
| 6,456,883 B1 | 9/2002 | Torgerson et al. |
| 6,471,645 B1 | 10/2002 | Warkentin et al. |
| 6,472,991 B1 | 10/2002 | Schulman et al. |
| 6,475,147 B1 | 11/2002 | Yost et al. |
| 6,475,170 B1 | 11/2002 | Doron et al. |
| 6,486,588 B2 | 11/2002 | Doron et al. |
| 6,504,286 B1 | 1/2003 | Porat et al. |
| 6,522,914 B1 | 2/2003 | Huvelle et al. |
| 6,567,700 B1 | 5/2003 | Turcott et al. |
| 6,574,510 B2 | 6/2003 | Von Arx et al. |
| 6,580,946 B2 | 6/2003 | Struble |
| 6,604,000 B2 | 8/2003 | Lu |
| 6,607,485 B2 | 8/2003 | Bardy |
| 6,609,023 B1 | 8/2003 | Fischell et al. |
| 6,615,083 B2 | 9/2003 | Kupper |
| 6,622,049 B2 | 9/2003 | Penner et al. |
| 6,628,989 B1 | 9/2003 | Penner et al. |
| 6,638,231 B2 | 10/2003 | Govari et al. |
| 6,644,322 B2 | 11/2003 | Webb |
| 6,654,638 B1 | 11/2003 | Sweeney |
| 6,675,049 B2 | 1/2004 | Thompson et al. |
| 6,699,186 B1 | 3/2004 | Wolinsky et al. |
| 6,702,847 B2 | 3/2004 | DiCarlo |
| 6,708,061 B2 | 3/2004 | Salo et al. |
| 6,708,065 B2 | 3/2004 | Von Arx et al. |
| 6,712,772 B2 | 3/2004 | Cohen et al. |
| 6,720,709 B2 | 4/2004 | Porat et al. |
| 6,720,887 B1 | 4/2004 | Zunti |
| 6,733,447 B2 | 5/2004 | Lai et al. |
| 6,738,667 B2 | 5/2004 | Deno et al. |
| 6,738,671 B2 | 5/2004 | Christophersom et al. |
| 6,743,173 B2 | 6/2004 | Penner et al. |
| 6,758,822 B2 | 7/2004 | Romano |
| 6,764,446 B2 | 7/2004 | Wolinsky et al. |
| 6,782,810 B2 | 8/2004 | Vilo |
| 6,783,499 B2 | 8/2004 | Schwartz |
| 6,792,308 B2 | 9/2004 | Corbucci |
| 6,792,311 B2 | 9/2004 | Fox et al. |
| 6,805,667 B2 | 10/2004 | Christopherson et al. |
| 6,809,507 B2 | 10/2004 | Morgan et al. |
| 6,824,512 B2 | 11/2004 | Warkentin et al. |
| 6,832,112 B1 | 12/2004 | Bornzin |
| 6,840,956 B1 | 1/2005 | Wolinsky et al. |
| 6,855,115 B2 | 2/2005 | Fonseca et al. |
| 6,859,665 B2 | 2/2005 | Ding et al. |
| 6,865,419 B2 | 3/2005 | Mulligan et al. |
| 6,868,346 B2 | 3/2005 | Larson et al. |
| 6,869,404 B2 | 3/2005 | Schulhauser et al. |
| 6,871,088 B2 | 3/2005 | Chinchoy |
| 6,885,889 B2 | 4/2005 | Chinchoy |
| 6,889,086 B2 | 5/2005 | Mass et al. |
| 6,895,265 B2 | 5/2005 | Silver |
| 6,907,285 B2 | 6/2005 | Denker et al. |
| 6,915,162 B2 | 7/2005 | Noren et al. |
| 6,926,670 B2 | 8/2005 | Rich et al. |
| 6,937,900 B1 | 8/2005 | Pianca et al. |
| 6,949,075 B2 | 9/2005 | Hatlesad et al. |
| 6,961,448 B2 | 11/2005 | Nichols et al. |
| 6,970,742 B2 | 11/2005 | Mann et al. |
| 6,978,182 B2 | 12/2005 | Mazar et al. |
| 6,985,773 B2 | 1/2006 | Von Arx et al. |
| 6,993,393 B2 | 1/2006 | Von Arx et al. |
| 7,003,350 B2 | 2/2006 | Denker et al. |
| 7,018,336 B2 | 3/2006 | Enegren et al. |
| 7,024,248 B2 | 4/2006 | Penner et al. |
| 7,033,322 B2 | 4/2006 | Silver |
| 7,035,684 B2 | 4/2006 | Lee |
| 7,047,065 B2 | 5/2006 | Kalgren et al. |
| 7,048,691 B2 | 5/2006 | Miele et al. |
| 7,060,030 B2 | 6/2006 | Von Arx et al. |
| 7,061,381 B2 | 6/2006 | Forcier et al. |
| 7,088,254 B2 | 8/2006 | Liebenow |
| 7,090,648 B2 | 8/2006 | Sackner et al. |
| 7,127,290 B2 | 10/2006 | Girouard et al. |
| 7,130,681 B2 | 10/2006 | Gebhardt et al. |
| 7,134,999 B2 | 11/2006 | Brauker et al. |
| 7,136,703 B1 | 11/2006 | Cappa et al. |
| 7,160,252 B2 | 1/2007 | Cho et al. |
| 7,181,268 B2 | 2/2007 | Sheldon et al. |
| 7,195,594 B2 | 3/2007 | Eigler et al. |
| 7,198,603 B2 | 4/2007 | Penner et al. |
| 7,200,439 B2 | 4/2007 | Zdeblick et al. |
| 7,203,545 B2 | 4/2007 | Schmitt et al. |
| 7,204,798 B2 | 4/2007 | Zdeblick et al. |
| 7,209,790 B2 | 4/2007 | Thompson et al. |
| 7,212,861 B1 | 5/2007 | Park et al |
| 7,214,189 B2 | 5/2007 | Zdeblick |
| 7,236,821 B2 | 6/2007 | Cates et al. |
| 7,248,923 B2 | 7/2007 | Maile et al. |
| 7,273,457 B2 | 9/2007 | Penner |
| 7,294,105 B1 | 11/2007 | Islam |
| 7,335,161 B2 | 2/2008 | Von Arx et al. |
| 7,399,313 B2 | 7/2008 | Brown et al. |
| 7,425,200 B2 | 9/2008 | Brockway et al. |
| 7,452,334 B2 | 11/2008 | Gianchandani et al. |
| 7,481,771 B2 | 1/2009 | Fonseca et al. |
| 7,742,815 B2 | 6/2010 | Sale et al. |
| 2001/0051766 A1 | 12/2001 | Gazdzinski |
| 2001/0051787 A1 | 12/2001 | Haller et al. |
| 2002/0022785 A1 | 2/2002 | Romano |
| 2002/0023123 A1 | 2/2002 | Madison |
| 2002/0042561 A1 | 4/2002 | Schulman et al. |
| 2002/0045812 A1 | 4/2002 | Ben-Haim et al. |
| 2002/0045836 A1 | 4/2002 | Alkawwas |
| 2002/0062086 A1 | 5/2002 | Miele et al. |
| 2002/0103454 A1 | 8/2002 | Sackner et al. |
| 2002/0120204 A1 | 8/2002 | Pfeiffer et al. |
| 2002/0126036 A1 | 9/2002 | Flaherty et al. |
| 2002/0147406 A1 | 10/2002 | von Segesser |
| 2002/0151770 A1 | 10/2002 | Noll, III et al. |
| 2002/0183628 A1 | 12/2002 | Reich et al. |

(56) References Cited

U.S. PATENT DOCUMENTS

| | | |
|---|---|---|
| 2002/0188323 A1 | 12/2002 | Penner et al. |
| 2003/0009204 A1 | 1/2003 | Amundson et al. |
| 2003/0023173 A1 | 1/2003 | Bratteli et al. |
| 2003/0045805 A1 | 3/2003 | Sheldon et al. |
| 2003/0060723 A1 | 3/2003 | Joo et al. |
| 2003/0114897 A1 | 6/2003 | Von Arx et al. |
| 2003/0136417 A1 | 7/2003 | Fonseca et al. |
| 2003/0181794 A1 | 9/2003 | Rini et al. |
| 2003/0191383 A1 | 10/2003 | Ben-Haim et al. |
| 2003/0199779 A1 | 10/2003 | Muhlenberg et al. |
| 2004/0032187 A1 | 2/2004 | Penner et al. |
| 2004/0044393 A1 | 3/2004 | Yarden et al. |
| 2004/0064133 A1 | 4/2004 | Miller et al. |
| 2004/0077937 A1 | 4/2004 | Yarden |
| 2004/0122484 A1 | 6/2004 | Hatlestad et al. |
| 2004/0122486 A1 | 6/2004 | Stahmann et al. |
| 2004/0152999 A1 | 8/2004 | Cohen et al. |
| 2004/0158163 A1 | 8/2004 | Cohen et al. |
| 2004/0167416 A1 | 8/2004 | Lee |
| 2004/0172081 A1 | 9/2004 | Wang |
| 2005/0056539 A1 | 3/2005 | Morgan et al. |
| 2005/0102002 A1 | 5/2005 | Salo et al. |
| 2005/0109338 A1* | 5/2005 | Stahmann et al. ....... 128/204.18 |
| 2005/0109339 A1 | 5/2005 | Stahmann et al. |
| 2005/0124904 A1 | 6/2005 | Roteliuk |
| 2005/0137490 A1 | 6/2005 | Scheiner et al. |
| 2005/0149143 A1 | 7/2005 | Libbus et al. |
| 2005/0154321 A1 | 7/2005 | Wolinsky et al. |
| 2005/0159639 A1 | 7/2005 | Skliar et al. |
| 2005/0159789 A1 | 7/2005 | Brockway et al. |
| 2005/0182330 A1 | 8/2005 | Brockway et al. |
| 2005/0187482 A1 | 8/2005 | O'Brien et al. |
| 2005/0192637 A1 | 9/2005 | Girouard et al. |
| 2005/0192844 A1 | 9/2005 | Esler et al. |
| 2005/0197585 A1 | 9/2005 | Brockway et al. |
| 2005/0215887 A1 | 9/2005 | Ben-Haim et al. |
| 2005/0242479 A1 | 11/2005 | Petisce et al. |
| 2005/0265999 A1* | 12/2005 | Bush et al. ................. 424/143.1 |
| 2005/0267379 A1 | 12/2005 | Pfeiffer et al. |
| 2005/0288727 A1 | 12/2005 | Penner |
| 2006/0009818 A1 | 1/2006 | Von Arx et al. |
| 2006/0031378 A1 | 2/2006 | Vallapureddy et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0089694 A1 | 4/2006 | Zhang et al. |
| 2006/0122522 A1 | 6/2006 | Chavan et al. |
| 2006/0136004 A1 | 6/2006 | Cowan et al. |
| 2006/0142651 A1 | 6/2006 | Brister et al. |
| 2006/0167359 A1 | 7/2006 | Bennett et al. |
| 2006/0167361 A1 | 7/2006 | Bennett et al. |
| 2006/0235323 A1 | 10/2006 | Hatib et al. |
| 2007/0043394 A1 | 2/2007 | Zhang et al. |
| 2007/0049977 A1 | 3/2007 | Von Arx et al. |
| 2007/0060959 A1 | 3/2007 | Salo et al. |
| 2007/0088221 A1 | 4/2007 | Stahmann |
| 2007/0129765 A1 | 6/2007 | Gilkerson et al. |
| 2007/0142727 A1 | 6/2007 | Zhang et al. |
| 2007/0142866 A1 | 6/2007 | Li et al. |
| 2007/0149890 A1 | 6/2007 | Li et al. |
| 2007/0161914 A1 | 7/2007 | Zdeblick et al. |
| 2007/0197921 A1 | 8/2007 | Cohen et al. |
| 2007/0282210 A1 | 12/2007 | Stern |
| 2007/0282381 A1 | 12/2007 | Li et al. |
| 2008/0015421 A1 | 1/2008 | Penner |
| 2008/0015651 A1 | 1/2008 | Ettori et al. |
| 2008/0021333 A1 | 1/2008 | Huelskamp |
| 2008/0021972 A1 | 1/2008 | Huelskamp et al. |
| 2008/0046037 A1 | 2/2008 | Haubrich et al. |
| 2008/0051843 A1 | 2/2008 | Li et al. |
| 2008/0071178 A1 | 3/2008 | Greenland et al. |
| 2008/0077440 A1 | 3/2008 | Doron |
| 2008/0243007 A1* | 10/2008 | Liao et al. .................... 600/486 |
| 2009/0201148 A1 | 8/2009 | Tran et al. |
| 2009/0204163 A1 | 8/2009 | Shuros et al. |
| 2009/0228078 A1 | 9/2009 | Zhang et al. |
| 2010/0056931 A1 | 3/2010 | Soffer et al. |
| 2010/0094144 A1 | 4/2010 | Doron |
| 2010/0222833 A1 | 9/2010 | Salo et al. |
| 2010/0324378 A1 | 12/2010 | Tran et al. |

FOREIGN PATENT DOCUMENTS

| | | |
|---|---|---|
| EP | 1266606 | 12/2002 |
| EP | 1169085 | 8/2004 |
| JP | 03-034196 | 2/1991 |
| JP | 10-055202 | 2/1998 |
| JP | 2004528152 | 9/2004 |
| JP | 2005-253657 | 9/2005 |
| JP | 2006-523120 | 10/2006 |
| JP | 2007-516796 | 6/2007 |
| JP | 2007-519441 | 7/2007 |
| WO | WO 83/03345 | 10/1983 |
| WO | WO 95/03086 | 2/1995 |
| WO | WO 95/27531 | 10/1995 |
| WO | WO 97/01986 | 1/1997 |
| WO | WO 97/18856 | 5/1997 |
| WO | WO 97/32519 | 9/1997 |
| WO | WO 97/33513 | 9/1997 |
| WO | WO 97/47236 | 12/1997 |
| WO | WO 98/26716 | 6/1998 |
| WO | WO 98/29030 | 7/1998 |
| WO | WO 99/17095 | 4/1999 |
| WO | WO 99/26530 | 6/1999 |
| WO | WO 99/34453 | 7/1999 |
| WO | WO 99/47205 | 9/1999 |
| WO | WO 99/55223 | 11/1999 |
| WO | WO 99/55225 | 11/1999 |
| WO | WO 99/59460 | 11/1999 |
| WO | WO 99/66988 | 12/1999 |
| WO | WO 00/16686 | 3/2000 |
| WO | WO 00/58744 | 10/2000 |
| WO | WO 01/28627 | 4/2001 |
| WO | WO 01/56467 | 8/2001 |
| WO | WO 01/74278 | 10/2001 |
| WO | WO 01/76367 | 10/2001 |
| WO | WO 01/85094 | 11/2001 |
| WO | WO 02/03347 | 1/2002 |
| WO | WO 02/32502 | 4/2002 |
| WO | WO 03/002243 | 1/2003 |
| WO | WO 03/096889 | 11/2003 |
| WO | WO2004012808 | 2/2004 |
| WO | WO 2004/091719 | 10/2004 |
| WO | WO2005000206 | 1/2005 |
| WO | WO 2005/065771 | 7/2005 |
| WO | WO2005063332 A1 | 7/2005 |
| WO | WO 2005/089638 | 9/2005 |
| WO | WO 2005/118056 | 12/2005 |
| WO | WO 2006/033812 | 3/2006 |
| WO | WO 2006/034183 | 3/2006 |
| WO | WO 2006/045073 | 4/2006 |
| WO | WO 2006/045074 | 4/2006 |
| WO | WO 2006/045075 | 4/2006 |
| WO | WO 2006/069215 | 6/2006 |
| WO | WO 2006/124833 | 11/2006 |
| WO | WO 2007/030474 | 3/2007 |
| WO | WO 2007/047287 | 4/2007 |
| WO | WO 2007/070794 | 6/2007 |
| WO | WO 2007/099533 | 9/2007 |
| WO | WO 2008/011570 | 1/2008 |
| WO | WO 2008/011592 | 1/2008 |
| WO | WO 2008/011593 | 1/2008 |
| WO | WO 2008/154145 | 12/2008 |

OTHER PUBLICATIONS

B. C. Penney et al., "Simplified electrode array for impedance cardiography," Medical & Biological Engineering & Computing, 1985, 23, p. 1-7.

(56) References Cited

OTHER PUBLICATIONS

B. Henderson et al., "Interaction of Photodynamic Therapy and Hyperthermia: Tumor Response and Cell Survival after Treatment of Mice in Vivo," Cancer Research, vol. 45, 6071 (Dec. 1985).

Bennett et al., "Subcutaneous pressure measurement as a surrogate for an external pressure reference for chronic implantable pressure monitoring," Journal of Cardial Failure, Churchill Livingstone, vol. 9, No. 5, p. S51, Oct. 1, 2003, abstract only.

Blacher, Jacques et al., "Aortic Pulse Wave Velocity as a Member of Cardiovascular Risk in Hypertensive Patients", Hypertension May 1999;33;1111-1117.

Bonnefoy E, Ninet J, Robin J, Leroux F, Boissonat P, Brule P, Champsaur G., 1994, Bipolar intramyocardial electrogram from an implanted telemetric pacemaker for the diagnosis of cardiac allograft rejection, Pacing Clin Electrophysiol, 17(11 Pt 2):2052-6.

Bourgeois, Maurice J. et al., "Continuous Determination of Beat-to-Beat Stroke Volume from Aortic pressure Pulses in the Dog", Circulation Research, vol. 39, pp. 15-24 (1976).

C. Hierold et al. (Germany, 1998) "Implantable Low Power Integrated Pressure Sensor System for Minimal Invasive Telemetric Patient Monitoring" IEEE, pp. 568-573.

Cohen, T.J. et al., "A Hemodynamically Responsive Antitachycardia System. Development and Basis for Design in Humans", Circulation 1990, vol. 82, No. 2, pp. 394-406, XP002560584.

Dipl.-Ing. Torsten Eggers et al. (Germany) "Implantable Telemetric Endosytem (ITES)" IMSAS Institut Fur Mikrosensoren-Aktuatoren Und-Systeme, 1998. 2 pp.

E R. Cosman et al. (Massachussetts, Apr. 1979) "A Telemetric Pressure Sensor for Ventricular Shunt Systems" Surgical Neurology vol. 11, No. 4, pp. 287-294.

El Gamal, M.I.H. et al., "Chronic Ventricular Pacing With Ventriculo-Atrial Conduction Versus Atrial Pacing in Three Patients With Symptomatic Sinus Bradycardia", PACE, vol. 4, Jan.-Feb. 1981, pp. 100-106.

Farzaneh-Far, Ramin et al., Usefulness of Noninvasive Estimate of Pulmonary Vascular Resistance to predict Mortality, Heart Failure, and Adverse Cardiovascular Events in Patients With Stable Coronary Artery Disease (from the Heart and Soul Study), The American Journal of Cardiology, vol. 101, Issue 6, Mar. 15, 2008, pp. 762-766.

Fink, Mathias, "Time Reversal of Ultrasonic Fields—Part I: Basic Principles", IEEE Transactions on Ultrasonics, Ferroelectrics, and Frequency Control, vol. 39, No. 5, Sep. 1992, pp. 555-566.

Fujiki, Akira et al., "Pacemaker Syndrome Evaluated by Cardiopulmonary Exercise Testing", PACE, vol. 13, Oct. 1990, pp. 1236-1241.

G.W.H. Schurink et al. (1998) "Late Endoleak After Endovascular Therapy for Abdominal Aortic Aneurysm" Eur. J. Vasc. Endovasc. Surg. vol. 17, pp. 448-450.

Gerhausser A, Reichel T, Neukomm P A, Bolz A, Hugel J, Schaldach M, 1997, Diagnosis of rejection after kidney transplantation by impedance spectroscopy with an implantable measuring system, Biomed Tech (Berl), 42 Suppl. 160-1.

GH White et al. (1997) "Endoleak Following Endoluminal Repair of AAA: Management Options and Patient Outcomes", J. Endovasc Surg, pp. 1-45.

Graichen et al., "Patient Monitoring System for Load Measurement with Spinal Fixation Devices," Med. Eng. Phys. 18, (1996), pp. 167-174.

Haas et al., "Photodynamic Effects of Dyes on Bacteria," Published in Mutation Research, 1979, vol. 60, pp. 1-11.

Hashima et al., "Nonhomogenous Analysis of Epicardial Strain Distributions During Acute Myocardial Ischemia in the Dog," J Biomech 1993, Jan 26: 19-35.

Hetzer R. et al., 1998, Daily non-invasive rejection monitoring improves long-term survival in pediatric heart transplantation, Ann. Thorac. Surg. (66):1343-1349.

International Search Report and Written Opinion issued in PCT/US2009/058242, mailed Dec. 30, 2009, 15 pages.

J.A. Parrish, "Photobiologic Consideration on Photoradiation Therapy," pp. 91-108, Porphyrin Photosensitization, Plenum Press, (1983).

K.E. Uhrich et al., "Synthesis and characterization of degradable poly(anhydride-co-imides)", Macromolecules, 1995, 28, 2184-93.

Karl E. Richard et al. (Germany, Jan. 1999) "First clinical results with a telemetric shunt-integrated ICP-sensor" Neurological Research vol. 21, pp. 117-120.

Labrousse and Satre, "Photodynamic Killing of Dictyostelium Discoideum Amoebae Mediated by 4',5'-Diiodoflurescin Isothiocyanate Dextran. A strategy for the isolation of Thermoconditional Endocytosis Mutants," published in Photochemistry and Photobiology, 1993, vol. 67, No. 3, pp. 531-537.

Mackay et al., "Bio-medical Telemetry: Sensing and Transmitting Biological Information from Animals and Man," John Wiley & Sons, Inc. New York (1970) pp. 244-245.

Pfitzmann R, Muller J, Grauhan O. Cohnert T, Hetzer R, Z Kardiol, 1998, Measuring bioelectric myocardial impedance as a non invasive method for diagnosis of graft rejection after heart transplantation, 87(4):258-266.

Pirolo J S, Shuman T S, Brunt E M, Liptay M J, Cox J L, Ferguson T B Jr., J Thoracic Cardiovasc Surg, 1992, Noninvasive detection of cardiac allograft rejection by prospective telemetric monitoring, 103(5):969-79.

Prof. Dr. Johannes Zacheja et al. (Germany, Sep. 1996) "An Implantable Microsystem for Biomedical Applications" Micro System Technologies 96, pp. 717-722.

Rozenman, Yoseph et al., "Wireless Acoustic Communication With a Miniature Pressure Sensor in the Pulmonary Artery for Disease Surveillance and Therapy of Patients With Congestive Heart Failure", Journal of the American College of Cardiology, 49:7, 2007, pp. 784-789.

S.K. Gupta et al. (1999) "Use of a Piezoelectric Film Sensor for Monitoring Vascular Grafts", The American Journal of Surgery, vol. 160, pp. 182-186.

Strickberger, S. Adam et al., "Extracardiac Ablation of the Canine Atrioventricular Junction by Use of High-Intensity Focused Ultrasound", Circulation, Jul. 13, 1999; downloaded from circ.ahajournals.org at ACS/GUIDANT on Jan. 4, 2008, pp. 203-208.

T. Chuter et al. (Sweden, Jan. 1997) "Aneurysm Pressure Following Endovascular Exclusion" Eur. J. Vasc. Endovasc. Surg. vol. 13, pp. 85-87.

T.A. Cochran et al. (1990) "Aortic Aneurysm Abdominal", Current Therapy in Adult Medicine, Fourth Edition.

Wesseling, KH et al., "Computation of Aortic Flow From Pressure in Humans Using a Nonlinear, Three-Element Model", Journal of Applied Physiology, vol. 74, Issue 5, pp. 2566-2573 (1993).

Wu, Francois et al., "Time Reversal of Ultrasonic Fields — Part II: Experimental Results", IEEE Transactions on Ultrasonics, Ferroelectrics, and Frequency Control, vol. 39, No. 5, Sep. 1992, pp. 567-578.

Z. Tang et al. (May 1995) "Data Transmission from an Implantable Biotelemeter by Load-Shift Keying Using Circuit Configuration Modulator" IEEE Transactions on Biomedical Engineering. vol. 42, No. 5, pp. 524-528.

Zacharoulis, A.A. et al., "Measurement of stroke vol. from pulmonary artery pressure record in man", British Heart Journal, 1975, vol. 37, pp. 20-25.

Humphrey, Chester B. et al., "An analysis of direct and indirect measurements of left atrial filling pressure", The Journal of Thoracic and Cardiovascular Surgery, vol. 71, No. 5, May 1976, pp. 643-647.

"Pulmonary Valve", from Wikipedia, the free encyclopedia, http://en.wikipedia.org/wiki/Pulmonary_valve.

"Cardiac Output", from Wikipedia, the free encyclopedia, http://en.wikipedia.org/wiki/Cardiac_output.

Takazawa et al., "Assessment of Vasoactive Agents and Vascular Aging by the Second Derivative of Photoplethysmogram Waveform", Hypertension, 1998, 32:365-370.

* cited by examiner

ASSESSMENT OF PULMONARY VASCULAR RESISTANCE VIA PULMONARY ARTERY PRESSURE

CROSS-REFERENCE TO RELATED APPLICATION

This application claims priority under 35 U.S.C. §119 to U.S. Provisional Application No. 61/116,174, filed on Nov. 19, 2008, entitled "Assessment of Pulmonary Vascular Resistance Via Pulmonary Artery Pressure," which is incorporated herein by reference in its entirety for all purposes.

TECHNICAL FIELD

The present invention relates generally to methods and systems for measuring hemodynamic parameters within a patient's body. More specifically, the present invention pertains to methods and systems for assessing pulmonary or systemic vascular resistance in a patient.

BACKGROUND

Pulmonary vascular resistance (PVR) is an important hemodynamic variable that affects prognosis and therapy in a wide range of cardiovascular and pulmonary conditions. In the diagnosis and treatment of cardiogenic pulmonary edema, for example, pulmonary vascular resistance can be used as an indicator for the distension of small pulmonary vessels, which typically occurs in early stages of heart decompensation in response to elevated left atrial pressures. In addition to the diagnosis and treatment of pulmonary edema, pulmonary vascular resistance can also be utilized as an indicator for other conditions, including pulmonary hypertension, pulmonary embolisms, and atelectasis. Since changes in pulmonary vascular resistance often occur in the early stage of diseases such as pulmonary edema, the periodic measurement of this parameter over time may provide a useful indicator for the early detection of an acutely worsening heart failure.

A variety of different techniques have been employed for measuring pulmonary vascular resistance. In one such method disclosed in U.S. Pat. No. 7,204,798, for example, an inflatable balloon catheter is used to induce a change in volume and/or pressure within a heart chamber during systole, and then inject a fluid into the heart chamber during diastole. A sensor is then used to measure the pressure and/or volume at a location within the heart (e.g., the left ventricle or aorta), which can then be used to compute various hemodynamic parameters, including pulmonary vascular resistance. While providing a means for calculating pulmonary vascular resistance, such methods typically require the insertion of a catheter within the body, and are therefore not useful in measuring long term trends that occur over longer periods of time.

SUMMARY

The present invention pertains to methods and systems for measuring pulmonary or systemic vascular resistance within a patient. An illustrative method of measuring pulmonary vascular resistance within a patient includes electrically inducing a retrograde pressure pulse within the patient's heart using a pulse generator, sensing at least one arterial pressure parameter in response to the retrograde pressure pulse using a pressure sensor located within a pulmonary artery, and computing a value of the change in pulmonary vascular resistance using the at least one sensed arterial pressure parameter. In some embodiments, data from multiple pulmonary vascular resistance assessments can be trended over a period of time to aid in detecting an underlying cardiovascular or pulmonary condition such as cardiogenic pulmonary edema.

An illustrative system for measuring pulmonary vascular resistance within a patient includes a pulse generator including at least one lead adapted to induce a retrograde pressure pulse within the left atrium of the heart, a pressure sensor implanted within a pulmonary artery and adapted to sense an arterial pressure waveform in response to the retrograde pressure pulse, and a processor adapted to compute a value of pulmonary vascular resistance using the sensed arterial pressure waveform. The processor may comprise a component or module of the pulse generator, the pressure sensor, or an external monitoring device in communication with the pulse generator and/or pressure sensor.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
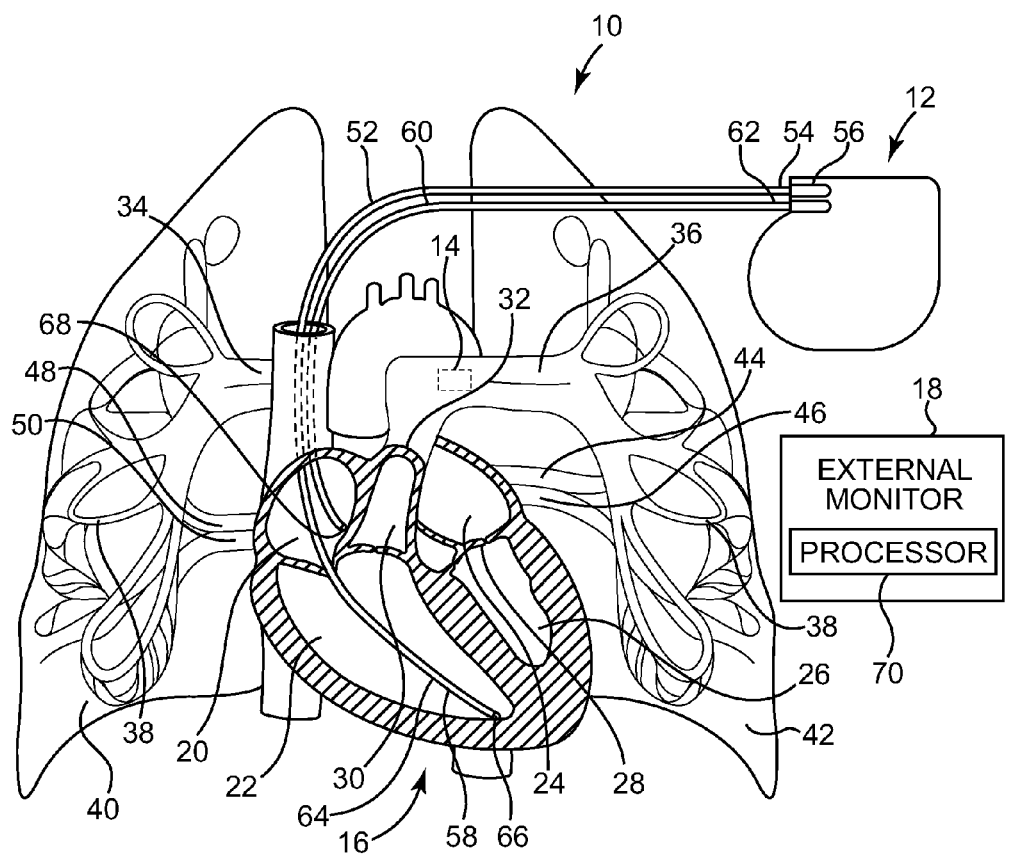
FIG. 1 is a schematic view of an illustrative system for measuring pulmonary vascular resistance within a patient's heart.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an illustrative system 10 for measuring pulmonary vascular resistance within a patient. In the embodiment of FIG. 1, the system 10 includes a pulse generator 12, a remote pressure sensor 14 implanted deeply within the patient's body such as in one of the pulmonary arteries leading from the patient's heart 16, and an external monitor 18 positioned at a location outside of the patient's body. The heart 16 includes a right atrium 20, a right ventricle 22, a left atrium 24, and a left ventricle 26. The left atrium 24 and left ventricle 26 are separated by the mitral valve 28. The right ventricle 22 includes an outflow tract 30 that delivers blood during ventricular systole to the main pulmonary artery 32, the right pulmonary artery 34 and the left pulmonary artery 36, which, in turn, flows into the pulmonary capillaries 38 of the lungs 40,42. The blood fed into the pulmonary capillaries 38 is oxygenated and returned back to the heart 16 via the pulmonary veins 44,46,48,50, as shown.

The pulse generator 12 can be implanted subcutaneously within the body, typically at a location such as in the patient's chest or abdomen, although other implantation locations are possible. In some embodiments, the pulse generator 12 is a dual-chamber pacemaker adapted to provide atrioventricular (AV) pacing therapy to the patient's heart 16. A number of leads 52,60 provide electrical stimulus to the right ventricle 24 and right atrium 22, which during normal pulse generator operation, can be used to synchronize the operation of the heart 16. A first lead 52 may be used for pacing ventricular contractions in the heart 16, and includes a proximal section 54 coupled to a header 56 of the pulse generator 12 and a distal section 58 implanted within the right ventricle 22 of the heart 16. A second lead 60, in turn, may be used for pacing atrial contractions in the heart 16, and includes a proximal section 62 coupled to the header 56 and a distal section 64 implanted within the right atrium 20 of the heart 16. An electrode 66,68 on each of the leads 52,60 can be configured to provide electrical stimulus energy for pacing the heart 16 and/or for sensing electrical activity occurring within the heart 16.

Although the system 10 depicts a dual-chamber pacemaker for use in providing atrioventricular pacing to the right atrium 20 and right ventricle 22 of the heart 16, in other embodiments, the system 10 may comprise a dual-chamber pacemaker adapted to pace the left atrium 24 and left ventricle 26 of the heart 16, or can comprise an implantable cardiac defibrillator (ICD) capable of providing electrical shocks to the heart 16. In some embodiments, the pulse generator 12 includes both pacing and defibrillation capabilities. The pacing therapy provided by the pulse generator 12 can be used to deliver bradycardia therapy, cardiac resynchronization therapy, or antitachycardia pacing therapy. In some embodiments, the pulse generator 12 is capable of pacing an atria to produce a retrograde pressure pulse within the heart 16, as discussed further herein, but does not provide pacing therapy.

During normal pulse generator operation, the leads 52,60 are configured to convey electrical signals between the pulse generator 12 and the heart 16. In those embodiments where the pulse generator 12 is a dual-chamber pacemaker operable in an AV pacing mode, for example, the leads 52,60 can be utilized to deliver electrical therapeutic stimulus energy for providing atrioventricular pacing to the heart 16. In those embodiments where the pulse generator 12 is operable in a defibrillation mode, one or more of the leads 52,60 can be utilized to deliver electrical shocks to the heart 16 in response to an event such as ventricle fibrillation. In an assessment mode of operation, and as further discussed herein, the leads 52,60 can also be utilized to periodically provide reverse, ventricular-atrial (VA) stimulus energy to the heart 16. This reverse, ventricular-atrial pacing can be utilized to induce a retrograde pressure pulse (i.e., a cannon wave) within the pulmonary arteries 32,34,36 that can be sensed by the pressure sensor 14 and used to calculate various hemodynamic properties, including pulmonary vascular resistance (PVR).

In some embodiments, the pressure sensor 14 can be implanted at a location within the right side of the heart 16 such as in the main pulmonary artery 32 or a branch of the main pulmonary artery such as the right or left pulmonary artery 34,36. In the illustrative system 10 of FIG. 1, for example, the pressure sensor 14 is implanted within the left pulmonary artery 36. An illustrative pressure sensor suitable for use in sensing arterial pressure within the body is described, for example, in U.S. Pat. No. 6,764,446, entitled "Implantable Pressure Sensors and Methods for Making and Using Them," the contents of which is incorporated herein by reference in its entirety. The pressure sensor 14 can be implanted at other locations within the pulmonary vasculature, and can be configured to perform one or more other designated functions, including the sensing of other physiological parameters within the body. Example physiological parameters that can also be sensed using the pressure sensor 14 can include, but are not limited to, blood flow, temperature, strain, acceleration, as well as various electrical, chemical and/or magnetic properties within the body.

Although the embodiment of FIG. 1 illustrates a remote pressure sensor 14 that is chronically implanted within the body, in other embodiments the pressure sensor 14 may comprise an acute or semi-acute sensing device that can be temporarily inserted into the patient's body for sensing arterial pressure. In one alternative embodiment, for example, the pressure sensor 14 can be coupled to or formed integrally with a catheter that can be temporarily inserted into the body for sensing blood pressure within a pulmonary artery or a systemic artery. Other devices that are temporarily or permanently insertable within the body can also be used for obtaining blood pressure measurements within a pulmonary artery or a systemic artery.

The pressure sensor 14 can be used in conjunction with the pulse generator 12 and/or the external monitor 18 to optimize pacing and/or defibrillation therapy, to predict decompensation of a heart failure patient, or to provide other monitoring and/or therapy functions. In certain embodiments, for example, the pressure sensor 14 can be utilized in conjunction with the pulse generator 12 to control atrioventricular (AV) pacing therapy to the patient based at least in part on a measure of pulmonary vascular resistance. Other devices such as a pulmonary sound sensor, satellite pacing device, or other sensing and/or therapy-delivering device may also be used in conjunction with the pulse generator 12 and pressure sensor 14.

The pressure sensor 14 can be configured to communicate with the pulse generator 12 and/or the external monitor 18 via a wireless or wired telemetry link. In some embodiments, for example, an acoustic telemetry link may be used to establish bi-directional wireless communications between the pressure sensor 14 and the pulse generator 12, and/or between the pressure sensor 14 and the external monitor 18. An example wireless telemetry system employing acoustic transducers is described, for example, in U.S. Pat. No. 7,024,248, entitled "Systems and Methods For Communicating With Implantable Devices," the contents of which are incorporated herein by reference in its entirety. Other types of telemetry modes such as RF, inductive, electromagnetic, and optical may also be utilized to establish a wireless telemetry link between the pressure sensor 14 and the pulse generator 12 and/or external monitor 18. In some embodiments, the pressure sensor 14 can communicate with other devices implanted within the body via either a wireless or wired telemetry link.

The external monitor 18 is configured to monitor an arterial pressure waveform signal transmitted by the pressure sensor 14. Based on this signal, a processor 70 within the external monitor 18 is configured to determine various hemodynamic parameters associated with the heart 16, including pulmonary vascular resistance. In some embodiments, other hemodynamic parameters can also be determined from the arterial pressure waveform sensed by the pressure sensor 14.

Although the external monitor 18 can be tasked to determine hemodynamic parameters such as pulmonary vascular resistance, in other embodiments other internal or external devices can be configured to compute such parameters. In one alternative embodiment, for example, the pulse generator 12 includes a processor adapted to compute hemodynamic parameters such as pulmonary vascular resistance based on the arterial pressure waveform signal from the pressure sensor 14. In another alternative embodiment, the pressure sensor 14 includes a processor adapted to compute pulmonary vascular resistance based on the sensed arterial pressure waveform signal.

Figure 2:
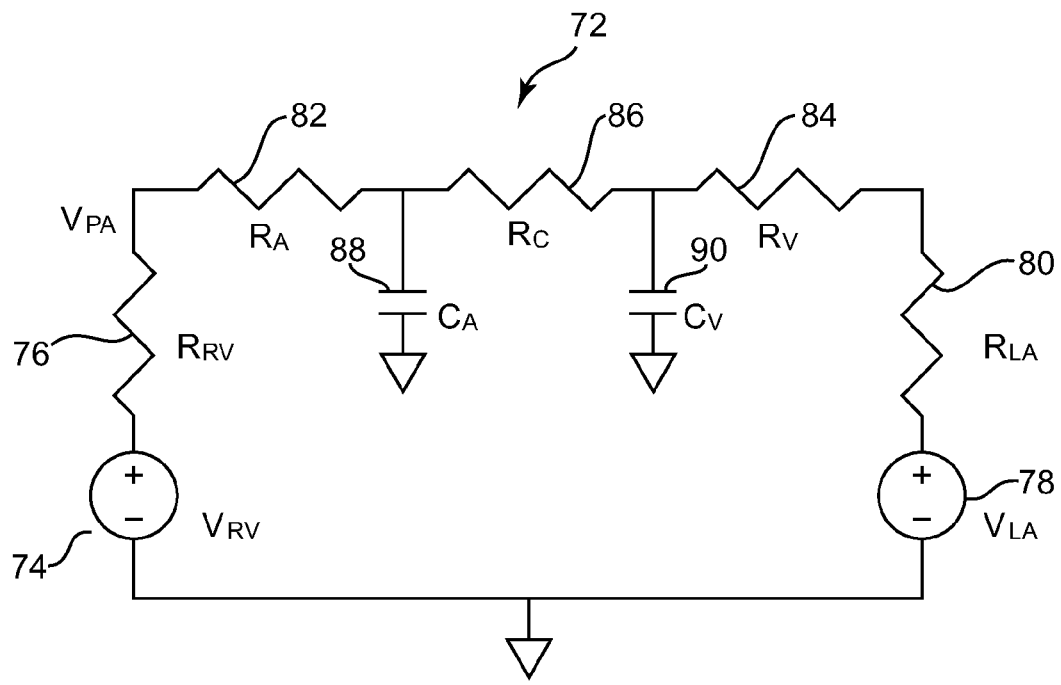
FIG. 2 is an equivalent electrical circuit modeling the pulmonary vasculature of a patient.

The vascular system can be modeled as an equivalent electrical circuit, which as discussed further herein, can be used by the processor 70 to compute a measure of pulmonary vascular resistance from a retrograde pressure pulse induced within the pulmonary arteries 32,34,36 when the pulse generator 12 operates in an assessment mode of operation. An illustrative equivalent electrical circuit 72 for modeling the pulmonary vascular system of a patient is shown in FIG. 2. The equivalent electrical circuit 72 may represent, for example, several analogous electrical elements that can be used to model the mechanical properties of the heart 16 and the pulmonary vasculature.

As shown in FIG. 2, the pump pressure and the mechanical resistance to the blood flow within the right ventricle 22 of the heart 16 can be modeled in the circuit 70, respectively, as a voltage source 74 ($V_{RV}$) and a resistor 76 ($R_{RV}$). The mechanical resistance of the blood flow 76 ($R_{RV}$) may represent, for example, the flow resistance to the pump pressure ($V_{RV}$) within the right ventricle 22 and pulmonic valve during a cardiac cycle. The pump pressure and the mechanical resistance to the blood flow within the left atrium 24 of the heart 16, in turn, can be modeled in the circuit 70, respectively, as a voltage source 78 ($V_{LA}$) and a resistor 80 ($R_{LA}$). The mechanical resistance of the blood flow ($R_{LA}$) may represent, for example, the flow resistance to the pump pressure ($V_{LA}$) entering the left atrium 24 from the pulmonary veins 44,46,48,50.

The flow resistance within the pulmonary vasculature, and in particular the pulmonary arteries 32,34,36 and the pulmonary veins 44,46,48,50, can be modeled in the circuit 70, respectively, as resistors 82 ($R_A$) and 84 ($R_V$). The flow resistance within the capillaries 38 of the lungs 40,42, in turn, can be modeled within the circuit 70 as a resistor 86 ($R_C$). The compliance of the pulmonary arteries 32,34,36 and the pulmonary veins 44,46,48,50 can be modeled in the circuit 70, respectively, as capacitors 88 ($C_A$) and 90 ($C_V$). The capacitors 86,88 may comprise, for example, modeled compliance values for the pulmonary arteries 32,34,36 and pulmonary veins 44,46,48,50.

A number of physiological assumptions can be used to simplify the mechanical to electrical relationship of the heart 16 and the pulmonary vasculature. For example, and as further shown in a simplified equivalent electrical circuit 92 in FIG. 3, the compliance values within the pulmonary vessels, including the pulmonary artery and pulmonary vein compliances ($C_A$), ($C_V$), can be ignored within the circuit 92. In addition, since the resistance within the pulmonary vascular tree is dominated primarily by the capillary resistance ($R_C$) due to their relatively small size and longer path, the resistances ($R_A$) and ($R_V$) can also be ignored within the circuit 92. The voltages ($V_{RV}$),($V_{LA}$) representing the pump pressure within the right ventricle 22 and left atrium 24 (i.e., $V_{RV}+V_{LA}$) may be further expressed as a single voltage source 94, as shown.

Figure 3:
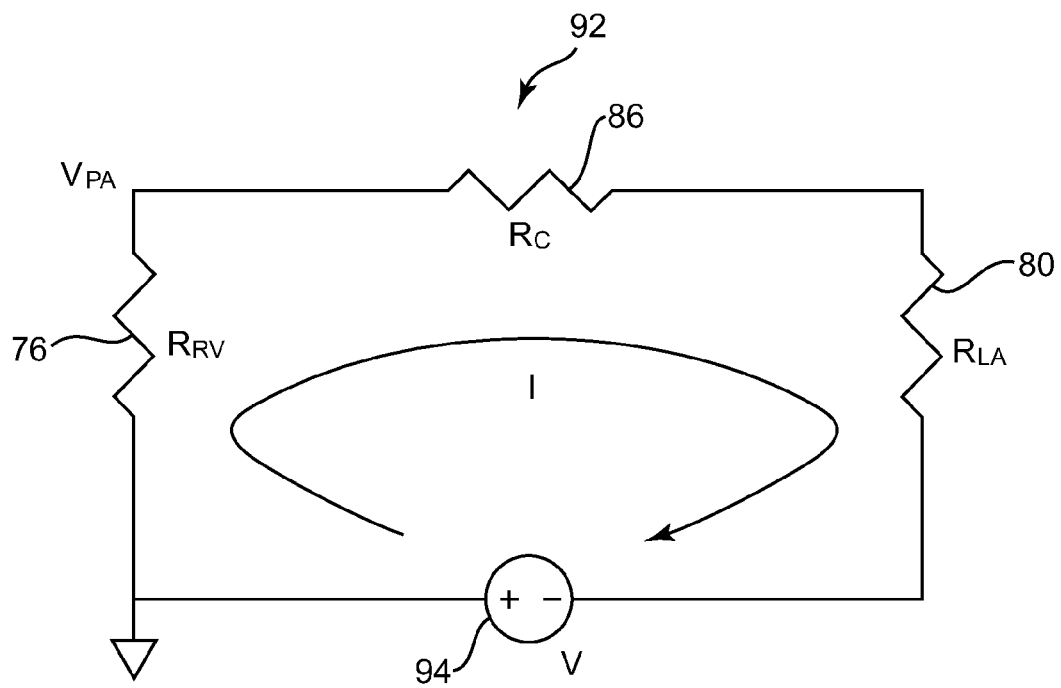
FIG. 3 is a simplified equivalent electrical circuit modeling the pulmonary vasculature of a patient.

From the simplified electrical circuit 92, the pump pressure within the pulmonary artery, represented as voltage "$V_{PA}$" in FIG. 3, can be determined using Ohm's law as follows:

$$V_{PA}=IR_{RV};\qquad(1)$$

where "I" in the above expression represents the electrical equivalent of blood flow within the pulmonary arteries 32,34, 36. A measure of the blood flow I within the circuit 92, in turn, can be determined from the following equation:

$$I=V/(R_{RV}+R_C+R_{RL}).\qquad(2)$$

From this value, the expression in (2) above can then be expressed as follows:

$$V_{PA}=VR_{RV}/(R_{RV}+R_C+R_{LA}).\qquad(3)$$

The above expression (3) can then be expressed in terms of the capillary resistance ($R_C$) as follows:

$$R_C=VR_{RV}/V_{PA}-R_{RV}-R_{LA}.\qquad(4)$$

To determine changes in capillary resistance ($R_C$), the pressure sensor 14 can be configured to take at least two measurements when a retrograde pressure pulse is induced by the pulse generator 12 during the assessment mode of operation, as reflected in the following two equations:

$$R_{C1}=V_1R_{RV1}/V_{PA1}-R_{RV1}-R_{LA1};\text{ and}\qquad(5)$$

$$R_{C2}=V_2R_{RV2}/V_{PA2}-R_{RV2}-R_{LA2};\qquad(6)$$

where $R_{C1}$ can be determined from a first pressure measurement taken by the pressure sensor 14 during ventricular-atrial (VA) pacing of the heart 16, and $R_{C2}$ can be determined from a second pressure measurement taken by the pressure sensor 14 during the ventricular-atrial (VA) pacing. Based on these sensed pressure measurements, the change in the capillary resistance $\Delta R_C$ can then be determined from the following expression:

$$\Delta_{RC}=R_{C1}-R_{C2}=V_1R_{RV1}/V_{PA1}-R_{RV1}-R_{LA1}-(V_2R_{RV2}/V_{PA2}-R_{RV2}-R_{LA2}).\qquad(7)$$

Assuming that $V_1=V_2$, $R_{RV1}=R_{RV2}$, and $R_{LA1}=R_{LA2}$, the above expression (7) can then be simplified as follows:

$$\Delta_{RC}=VR_{RV}(1/V_{PA1}-1/V_{PA2}).\qquad(8)$$

The term "$V(R_{RV})$" in the above expression (8) may be assumed to be a known constant, K, yielding:

$$\Delta_{RC}=K(1/V_{PA1}-1/V_{PA2}).\qquad(9)$$

As can be seen from equation (9) above, a change in pulmonary capillary resistance ($\Delta_{RC}$) can thus be estimated based on the pulse pressure measurements (i.e., $V_{PA1}, V_{PA2}$) sensed by the pressure sensor 14 during the assessment mode of operation when the pulse generator 12 provides ventricular-atrial pacing to induce a retrograde pressure pulse within the pulmonary arteries 32,34,36. Since the change in capillary resistance ($\Delta_{RC}$) correlates to the change in pulmonary vascular resistance due to the dominance of the capillary resistance to the overall resistance within the pulmonary vasculature (i.e., $R_C \gg (R_A+R_V)$), an estimate of the change in pulmonary vascular resistance can thus be determined by measuring changes in arterial pressure that occur within the pulmonary arteries 32,34,36.

Figure 4:
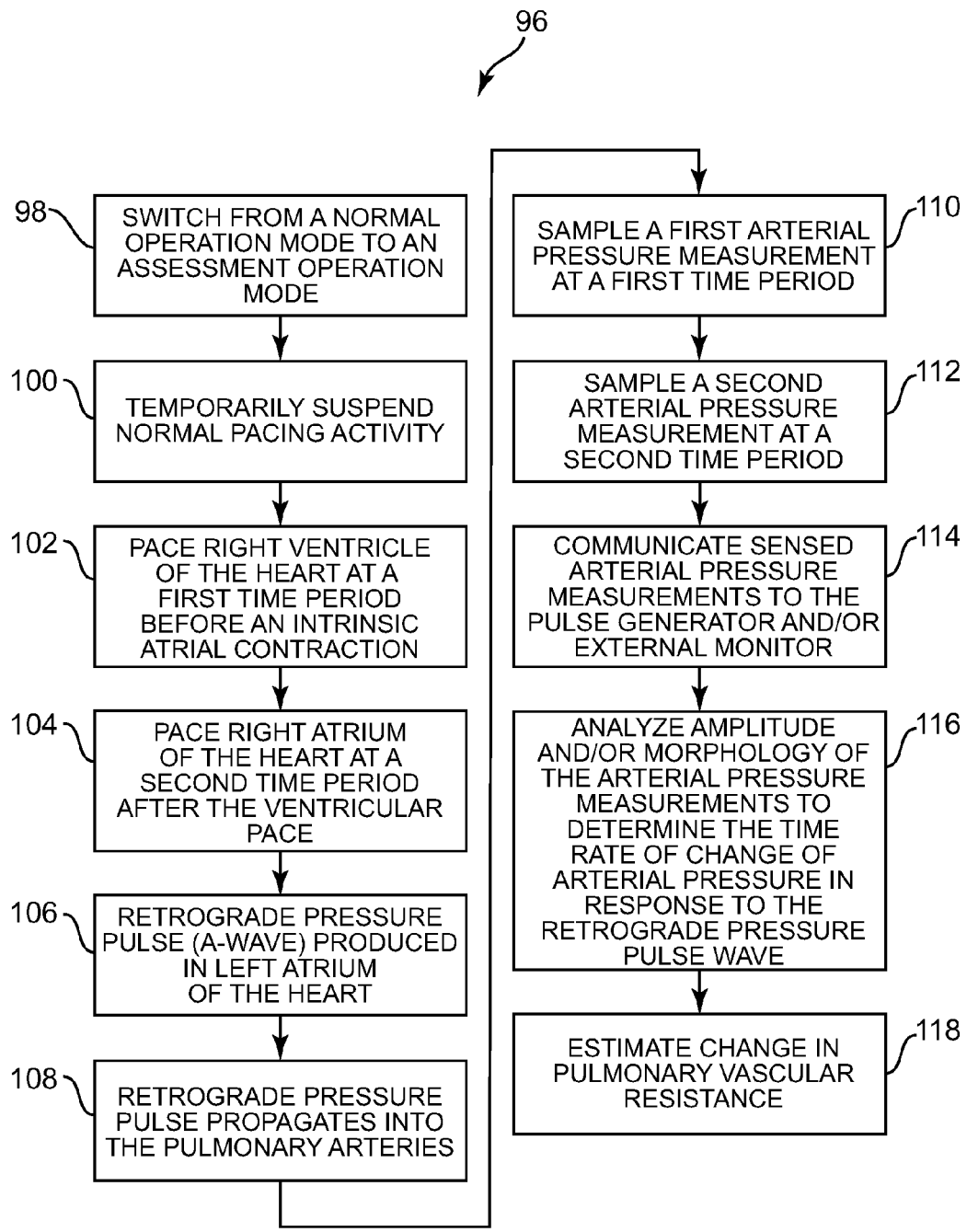
FIG. 4 is a flow chart showing an illustrative method of measuring pulmonary vascular resistance within a patient using the system of FIG. 1.

FIG. 4 is a flow chart showing an illustrative method 96 of measuring pulmonary vascular resistance within a patient using the system 10 of FIG. 1. Method 96 may represent, for example, an algorithm or routine used by the external monitor processor 70 of FIG. 1 to compute a measure of pulmonary vascular resistance based on a retrograde pressure pulse sensed by the pressure sensor 14. Alternatively, and in other embodiments, the method 96 may represent an algorithm or routine run by another device located inside or outside of the patient's body. In some embodiments, for example, the method 96 may be performed by the pulse generator 12, another implant located within the body, or by the pressure sensor 14.

As shown in FIG. 4, the method 96 may begin generally at block 98, when the pulse generator 12 switches from a normal mode of operation to an assessment mode of operation used to compute pulmonary vascular resistance. In some embodiments, for example, the pulse generator 12 may switch from the normal operation mode to the assessment operation mode in response to a command or signal received from the external monitor 18. In other embodiments, the pulse generator 12 may switch to the assessment mode at a predetermined time period (e.g., once a day, once a week, one a month, etc.) programmed within the pulse generator 12.

When in the assessment mode, the pulse generator 12 may temporarily suspend normal pacing activity provided by the leads 52,60 (block 100). Once suspended, the pulse generator 12 is then configured to electrically induce a retrograde pressure pulse within the left atrium 24 of the patient's heart 16. In certain embodiments, for example, the retrograde pressure pulse is induced by first pacing the right ventricle 22 using the ventricular lead 52 at a first time period immediately before an intrinsic atrial contraction (block 102). For example, in some embodiments the ventricular lead 52 can be configured to deliver an electrical pacing stimulus at a time period of about 150 ms before an intrinsic atrial contraction.

Subsequent to the first, ventricular pace, the pulse generator 12 may next pace the right atrium 24 at a second time period using the atrial lead 60 (block 104). In certain embodiments, for example, the atrial lead 60 can be configured to deliver an electrical pacing stimulus at a period of about 100 ms after the first, ventricular pace, which causes the right and left atria 22,24 to contract. Since the mitral valve 28 will be closed during the atrial contraction as a result of the atrial pace, a retrograde pressure wave (i.e., an a-wave) is produced within the left atrium 24 (block 106). This retrograde pressure pulse wave then propagates through the pulmonary veins 44,46,48,50 and pulmonary capillaries 38 and back into the pulmonary arteries 32,34,36 (block 108).

The pressure sensor 14 can be prompted to take one or more arterial pressure measurements to determine the amplitude and morphology characteristics of the retrograde pressure pulse wave, which as discussed above with respect to FIGS. 2-3, can be correlated with changes in the pulmonary vascular resistance. In one embodiment, for example, the pressure sensor 14 may sample a first arterial pressure parameter within the pulmonary artery at a first time period (block 110) subsequent to the VA pacing provided by the pulse generator 12. The first arterial pressure parameter may represent, for example, $V_{PA1}$ in equation (9) discussed herein with respect to FIGS. 2-3. The pressure sensor 14 may then sample a second arterial pressure parameter at a second time period (block 112) after the first sampled arterial pressure parameter. The second arterial pressure parameter may represent, for example, $V_{PA2}$ in equation (9) discussed above.

The pressure sensor 14 can be configured to communicate the sensed arterial pressure measurements to the pulse generator 12 and/or the external monitor 18 (block 114). The pulse generator 12 and/or external monitor 18 may then analyze the amplitude and/or morphology of the arterial pressure measurements taken to determine the time rate of change of the arterial pressure waveform in response to the retrograde pressure pulse wave (block 116). Based on this change, a value of the pulmonary vascular resistance is then estimated (block 118). In certain embodiments, for example, the change in pulmonary vascular resistance may be estimated by correlating the pulmonary capillary resistance value ($\Delta_{RC}$) computed using equation (9) discussed above with a correlation factor. In certain embodiments, the pressure pulse (i.e., conduction) velocity alone can be provide a useful diagnostic parameter for assessing a cardiovascular or pulmonary condition.

In some embodiments, the detection of elevated pulmonary arterial pressures without a significant increase in pulmonary vascular resistance can also be used to exclude the diagnosis of certain conditions such as chronic obstructive pulmonary disease (COPD), worsening pulmonary hypertension, or other non-cardiogenic conditions that cause an increase in pulmonary arterial pressure. In some cases, an increase in pulmonary vascular resistance in conjunction with other sensed parameters can also be used to diagnose certain conditions. For example, an increase in pulmonary vascular resistance in conjunction with pulmonary artery distension may be used to aid in diagnosing a condition such as chronic obstructive pulmonary disease (COPD) or an increase in pulmonary hypertension.

In some embodiments, changes in the systemic pressure morphology can also be measured to determine the systemic vascular resistance (SVR) and/or systemic conduction velocities. The pacing provided to the right atrium 22 of the heart 16 at step 104 also causes the right atrium 22 to simultaneously contract along with the left atrium 24, producing a retrograde pressure pulse from the right atrium 22 that propagates into the systemic arteries and veins. A pressure sensor implanted within the aorta, the peripheral vasculature, or the superior vena cava can be used to take pressure measurements to determine the amplitude and morphology characteristics of the retrograde pressure pulse wave induced within the systemic vasculature. In some embodiments, for example, the pressure sensor may sample first and second pressure parameters at a location such as the aorta or the superior vena cava, and then determine a time rate of change in the pressure waveform in response to the retrograde pressure pulse wave. Based on this change, a value of the systemic vascular resistance and/or systemic conduction velocity can then be estimated.

Figure 5A:
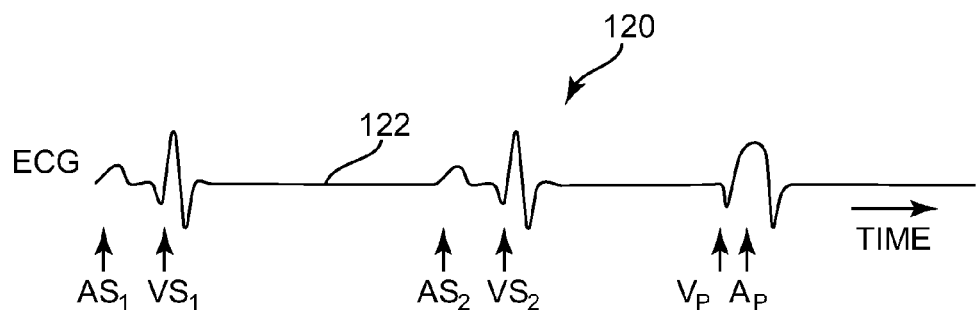
FIGS. 5A-5B are several graphs showing an illustrative ECG waveform and pulmonary artery pressure waveform in response to pacing signals provided by the pulse generator during the assessment mode of operation.
Figure 5B:
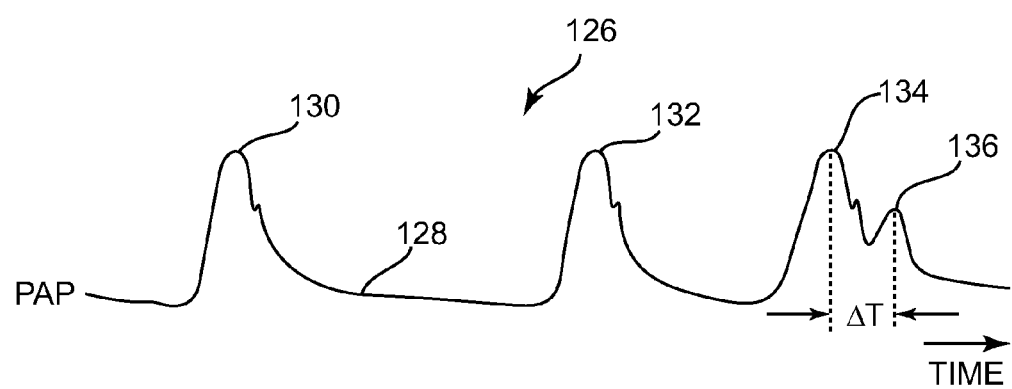

FIGS. 5A-5B are several graphs showing an illustrative electrocardiograph (ECG) waveform and pulmonary artery pressure waveform in response to pacing signals provided by the pulse generator 12 during the assessment mode of operation. The electrical activity of the heart 16 in response to several AV and VA pacing pulses provided by the pulse generator 12 is depicted in a first graph 120 in FIG. 5A. FIG. 5A may represent, for example, a sensed ECG waveform 122 of the heart 16 in response to several pacing pulses provided to the heart 16 using the dual-chamber pacing leads 52,60 of the system 10 of FIG. 1.

During normal device operation, the pulse generator 12 may provide several atrioventricular (AV) pacing pulses $A_{S1}$, $V_{S1}$, and $A_{S2}$,$V_{S2}$ to the heart 16, which as shown on the ECG waveform 122, results in the characteristic P-wave and QRS complex electrical signature of the heart 16. In response to normal AV pacing, and as further shown in the graph 126 of FIG. 5B, the pressure sensor 14 senses an arterial pressure waveform 128 within a pulmonary artery 32,34,36. As shown from the arterial pressure waveform 128, the pulmonary artery pressure increases at points 130 and 132 in response to the AV pacing pulses $A_{S1}$,$V_{S1}$, and $A_{S2}$,$V_{S2}$ provided by the pulse generator 12.

When the assessment mode of operation is initiated, the pulse generator 12 provides retrograde VA conduction by supplying a first, ventricular pacing pulse $V_P$ to the right ventricle 22 of the heart 16 at a point in time immediately prior to an intrinsic atrial contraction, causing the mitral valve 28 to close and the right ventricle 22 and left ventricle 26 to contract. A second pacing pulse $A_P$ following the first, ventricular pacing pulse $V_P$ may then be provided to the right atrium 20, causing the right atrium 20 and left atrium 24 to contract and produce a retrograde pressure pulse wave that propagates through the pulmonary veins 44,46,48,50, the pulmonary capillaries 38, and back into the pulmonary arteries 32,34,36.

As can be further seen in FIG. 5B, the ventricular pace $V_P$ provided by the ventricular lead 52 causes the arterial pressure waveform 128 to initially spike at point 134 (i.e., systolic peak pressure) as a result of the ventricular contraction in the right ventricle 22. The pressure pulse induced in the left atrium 24 during ventricular systole provides a transient change in the pressure in the pulmonary arteries 32,34,36. At a second section 136 of the arterial pressure waveform 128, once the retrograde pressure pulse wave propagates from the left atrium 24 back to the pulmonary arteries 32,34,36, the morphology of the retrograde pressure pulse wave changes as a result of the right ventricular systolic pulse caused by the ventricular pace $V_P$. The morphology of the arterial pressure waveform 128 at this section 136 can be analyzed in order to determine a measure of pulmonary vascular resistance within the pulmonary vasculature. In one embodiment, for example, the method 96 of FIG. 4 can be used to obtain an estimate of the change in pulmonary vascular resistance by sampling a first arterial pressure measurement and a second arterial pressure measurement, computing a value of the change in pulmonary capillary resistance induced by the retrograde pressure pulse based on the first and second arterial pressure measurements, and then determining a value of the change in pulmonary vascular resistance from the change in capillary resistance.

In some embodiments, the morphology of the pulmonary artery pressure waveform 128 may be used to identify changes in vascular resistance by analyzing the timing of the retrograde pressure wave. The timing of the retrograde pressure wave indicates the pressure pulse velocity, which, in turn, is correlated to the vascular resistance. The time period at which the reflected wave reaches the pressure sensor can be seen in FIG. 5B as the difference in time $\Delta T$ between the systolic peak pressure 134 and the reflected peak pressure at 136. In general, the shorter the time difference $\Delta T$ between the ventricular systolic peak pressure (134) and the reflected peak pressure (136), the higher the vascular resistance. Conversely, the longer the time difference $\Delta T$ between the ventricular systolic peak pressure (134) and the reflected peak pressure (136), the lesser the vascular resistance.

Figure 6:
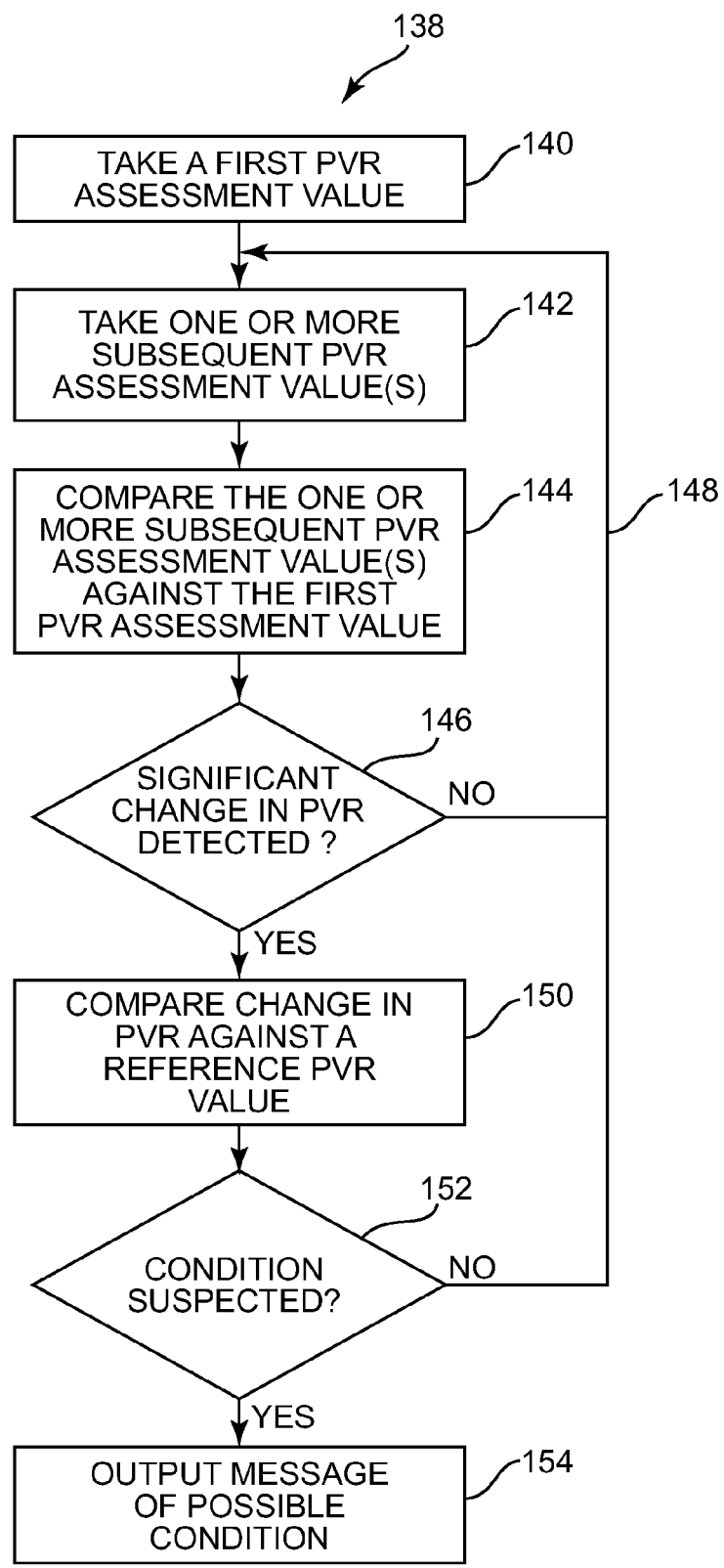
FIG. 6 is a flow chart showing an illustrative method of trending data from multiple pulmonary vascular resistance assessments taken over an extended period of time for detecting a cardiovascular or pulmonary condition within a patient.

FIG. 6 is a flow chart showing an illustrative method 138 of trending data from multiple pulmonary vascular resistance assessments taken over a period of time. In some embodiments, for example, the method 138 can be used by the system 10 of FIG. 1 to permit the early detection of an acutely worsening heart failure due to conditions such as cardiogenic pulmonary edema, pulmonary hypertension, pulmonary embolisms, and/or atelactasis. The method 138 can also be used to detect other conditions where changes in pulmonary vascular resistance can occur over time. Although the method 138 is described with respect to pulmonary vascular resistance assessments, in other embodiments the method 138 may also be used to detect and analyze trends in systemic vascular resistance using a similar approach.

The method 138 may begin generally at block 140, in which a first PVR assessment is made by the system 10 to determine an initial pulmonary vascular resistance (PVR) value. In some embodiments, for example, the first PVR assessment value may comprise a measure of the change in pulmonary vascular resistance occurring in response to a retrograde pressure pulse induced by ventricular-atrial conduction. In some embodiments, the first PVR assessment value may comprise a running average of the change in pulmonary vascular resistance.

Subsequent to the initial assessment, the system 10 may then determine one or more subsequent pulmonary vascular resistance assessment values (block 142), which is/are then compared against the first PVR assessment value (block 144) to determine whether a change has occurred indicating the onset of an underlying condition such as cardiogenic pulmonary edema. In some embodiments, for example, a second PVR assessment value may be taken at a much later period of time (e.g., one month) after the initial PVR assessment value and then compared against the initial PVR assessment value to determine whether a significant change has occurred in the PVR over that time period. If no change is detected at decision block 146), the system 10 continues to take additional PVR assessments 148, which can then be compared against one or more prior assessment values. If a significant change in PVR is detected, the system 10 may next compare that value against a reference PVR value (block 150) and determine whether the change in PVR is sufficiently large to indicate the presence of an underlying condition (block 152). If not sufficiently large, the system 10 may take one or more additional PVR assessment values. Otherwise, if the system 10 determines that the change in PVR is sufficiently large (e.g., greater than 5%), then the system 10 may trigger a flag causing the pulse generator 12 and/or external monitor 18 to output a message or alert to the patient or caregiver indicating that an underlying condition is suspected (block 154).

Figure 7:
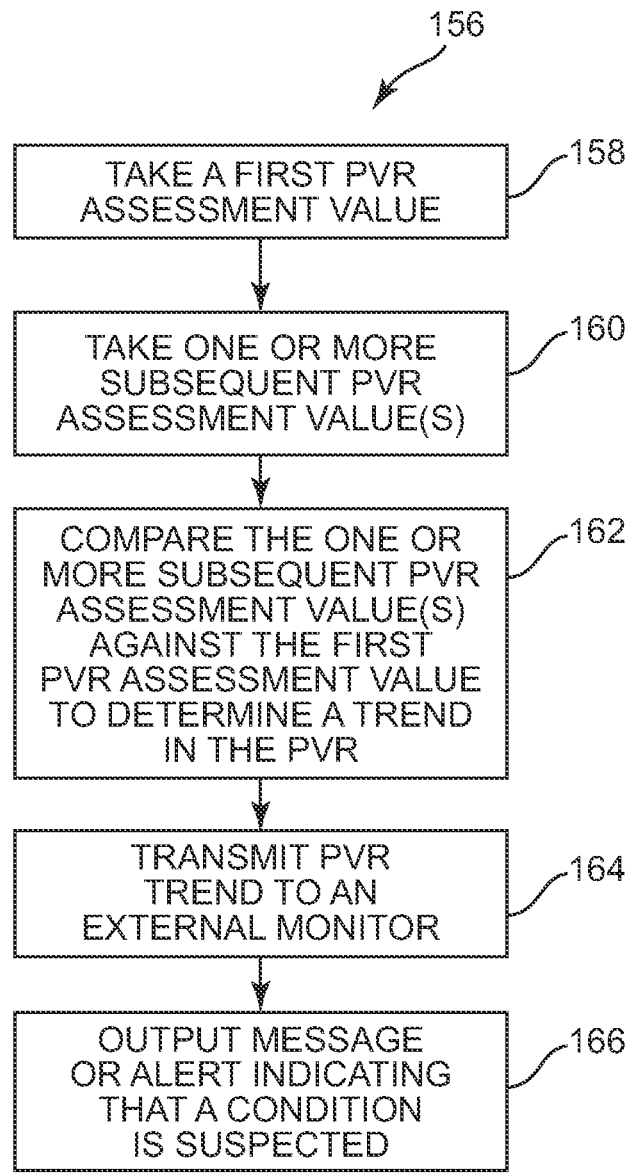
FIG. 7 is a flow chart showing an illustrative method of producing a trend of pulmonary vascular resistance.

FIG. 7 is a flow chart showing another illustrative method 156 of producing a trend of pulmonary vascular resistance. The method 156 may begin generally at block 158, in which a first PVR assessment is made by the system 10 to determine an initial pulmonary vascular resistance (PVR) value. Subsequent to the initial assessment, the system 10 may then determine one or more subsequent pulmonary vascular resistance values (block 160). The one or more subsequent pulmonary vascular resistance values are then compared against the first PVR assessment value to determine a trend in the PVR (block 162). An example trend in the PVR may be, for example, a significant increase or decrease in PVR over a predetermined period of time.

In some embodiments, the PVR trend is transmitted to an external monitor (block 162) located on or near the patient (e.g., a programming unit) or at a location remote from the patient (e.g., a remote monitoring unit). From the PVR trend, the external monitor may then determine whether a condition is suspected (block 164). If a condition is suspected, the external monitor may then output a message or alert to the patient or caregiver indicating that an underlying condition is suspected (block 166).

In some embodiments, the PVR trend(s) can be used for controlling the sensitivity and/or specificity of the message or alert provided to the patient or caregiver. For example, if a PVR trend indicates a condition such as heart decompensation, the external monitor may increase the sensitivity at which the message or alert is triggered in order to alert the patient or caregiver of further possible heart decompensation. The external monitor may also adjust the level of specificity of the message or alert generated to inform the patient or clinician that the particular type of condition suspected is heart decompensation. The adjustment of the sensitivity and specificity of the alert or message generated may then be used as an aid by the clinician in performing additional testing or diagnostics on the patient to confirm the suspected condition.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method of measuring pulmonary vascular resistance within a patient, the method comprising:
   electrically inducing a retrograde pressure pulse from the left atrium of the heart by using a pulse generator to electrically stimulate the heart to cause the mitral valve to be closed during atrial systole;
   sensing at least one arterial pressure parameter in response to the retrograde pressure pulse using a pressure sensor located within a pulmonary artery of the patient; and
   computing a value of the change in pulmonary vascular resistance using the at least one sensed arterial pressure parameter.

2. The method of claim 1, wherein electrically inducing a retrograde pressure pulse from the left atrium of the patient's heart includes:
   providing an electrical stimulus to a ventricle of the heart at a first time period prior to an intrinsic atrial contraction; and
   providing an electrical stimulus to an atrium of the heart at a second time period subsequent to the first time period.

3. The method of claim 1, wherein sensing at least one arterial pressure parameter includes sensing a first arterial pressure parameter and a second arterial pressure parameter.

4. The method of claim 3, wherein computing a value of the change in pulmonary vascular resistance includes comparing the first arterial pressure parameter against the second arterial pressure parameter.

5. The method of claim 4, wherein computing a value of the change in pulmonary vascular resistance in response to the retrograde pressure pulse includes comparing an amplitude of the first arterial pressure parameter against an amplitude of the second arterial pressure parameter.

6. The method of claim 4, wherein computing a value of the change in pulmonary vascular resistance in response to the retrograde pressure pulse includes computing a measure of the change in pulmonary capillary resistance in response to the retrograde pressure pulse.

7. The method of claim 1, wherein computing a value of the change in pulmonary vascular resistance in response to the retrograde pressure pulse includes analyzing the morphology of the at least one sensed arterial pressure parameter.

8. The method of claim 1, wherein computing a value of the change in pulmonary vascular resistance in response to the retrograde pressure pulse is performed by an external monitor in wireless communication with the pressure sensor.

9. The method of claim 1, wherein computing a value of the change in pulmonary vascular resistance in response to retrograde pressure pulse is performed by a processor of the pulse generator.

10. The method of claim 1, wherein computing a value of the change in pulmonary vascular resistance in response to the retrograde pressure pulse is performed by a processor of the pressure sensor.

11. The method of claim 1, further including computing one or more additional values of the pulmonary vascular resistance, and comparing the one or more additional values against a previously computed value to determine a change in pulmonary vascular resistance.

12. The method of claim 1, further including trending data from multiple pulmonary vascular resistance values taken over a period of time.

13. The method of claim 12, wherein trending data from multiple pulmonary vascular resistance values over a period of time includes:
   taking a first pulmonary vascular resistance assessment at a first time period within the patient;
   taking a second pulmonary vascular resistance assessment at a second time period subsequent to the first time period;
   comparing the second pulmonary vascular resistance assessment against the first pulmonary vascular resistance assessment and determining a trend in the pulmonary vascular resistance; and
   detecting a cardiac or pulmonary condition within the patient based on the first and second pulmonary vascular resistance assessments.

14. A method of measuring pulmonary or systemic vascular resistance within a patient, the method comprising:
   electrically inducing a retrograde pressure pulse from an atrium of the heart by using a pulse generator to electrically stimulate the heart to cause the mitral valve to be closed during atrial systole;
   sensing at least one pressure parameter in response to the retrograde pressure pulse using a pressure sensor located within a body lumen of the patient; and
   computing a value of pulmonary or systemic vascular resistance using the at least one sensed pressure parameter.

15. A system for measuring pulmonary vascular resistance within a patient, the system comprising:
   a pulse generator including at least one lead adapted to induce a retrograde pressure pulse from the left atrium of the heart by electrically stimulating the heart to cause the mitral valve to be closed during atrial systole;
   a pressure sensor adapted to sense an arterial pressure waveform within a pulmonary artery; and
   a processor adapted to compute a value of pulmonary vascular resistance in response to the retrograde pressure pulse based the sensed arterial pressure waveform.

16. The system of claim 15, wherein the at least one lead includes:
   a first lead adapted to provide an electrical pacing stimulus to a ventricle of the patient's heart; and
   a second lead adapted to provide an electrical pacing stimulus to an atrium of the patient's heart.

17. The system of claim 15, wherein the processor is a component of the pulse generator.

18. The system of claim 15, wherein the processor is a component of an external monitoring device in wireless communication with the pressure sensor.

19. The system of claim 15, wherein the pulse generator is operable between a normal mode of operation for providing atrioventricular pacing to the patient's heart and an assessment mode of operation for inducing the retrograde pressure pulse within the pulmonary artery.

20. The system of claim 15, wherein the processor is configured to compute a value of a change in pulmonary vascular resistance in response to the retrograde pressure pulse from at least two arterial pressure parameters sensed by the pressure sensor.

21. The system of claim 15, wherein the processor is configured to compute a value of a change in pulmonary vascular resistance in response to the retrograde pressure pulse by computing a change in pulmonary capillary resistance.

22. The system of claim 15, wherein the processor is configured to compute a value of a change in pulmonary vascular resistance in response to the retrograde pressure pulse by analyzing the morphology of the arterial pressure waveform.

* * * * *